(12) United States Patent
Keast et al.

(10) Patent No.: US 7,393,330 B2
(45) Date of Patent: Jul. 1, 2008

(54) ELECTROSURGICAL DEVICE HAVING HOLLOW TISSUE CUTTING MEMBER AND TRANSDUCER ASSEMBLY

(75) Inventors: Thomas Keast, Sunnyvale, CA (US); Christopher L. Willink, Campbell, CA (US); Edmund J. Roschak, Mission Viejo, CA (US); Dave Haugaard, San Jose, CA (US); David Thompson, San Jose, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 0 days.

(21) Appl. No.: 11/357,244

(22) Filed: Feb. 16, 2006

(65) Prior Publication Data

US 2006/0142672 A1 Jun. 29, 2006

Related U.S. Application Data

(63) Continuation of application No. 10/079,605, filed on Feb. 21, 2002, now Pat. No. 7,022,088, which is a continuation-in-part of application No. 09/946,706, filed on Sep. 4, 2001, now Pat. No. 6,749,606, which is a continuation-in-part of application No. 09/908,087, filed on Jul. 18, 2001, now abandoned, which is a continuation of application No. 09/633,651, filed on Aug. 7, 2000, now Pat. No. 6,692,494.

(60) Provisional application No. 60/269,130, filed on Feb. 14, 2001, provisional application No. 60/176,141, filed on Jan. 14, 2000, provisional application No. 60/147,528, filed on Aug. 5, 1999.

(51) Int. Cl.
*A61B 18/18* (2006.01)

(52) U.S. Cl. .............................. 601/2; 606/41

(58) Field of Classification Search ................. 600/427, 600/439, 453, 543; 606/27, 28, 32–34, 41; 601/2, 3
See application file for complete search history.

(56) References Cited

U.S. PATENT DOCUMENTS

| 3,433,226 | A | 3/1969 | Boyd |
|---|---|---|---|
| 3,556,079 | A | 1/1971 | Omizo |
| 3,565,062 | A | 2/1971 | Kuris |
| 3,779,234 | A | 12/1973 | Eggleton et al. |
| 3,823,717 | A | 7/1974 | Pohlman et al. |
| 3,942,530 | A | 3/1976 | Northeved |
| 4,249,539 | A | 2/1981 | Vilkomerson et al. |
| 4,249,541 | A | 2/1981 | Pratt |
| 4,319,580 | A | 3/1982 | Colley et al. |

(Continued)

FOREIGN PATENT DOCUMENTS

DE 3821836 A1 1/1990

(Continued)

*Primary Examiner*—Roy D. Gibson
*Assistant Examiner*—Aaron Roane
(74) *Attorney, Agent, or Firm*—Levine Bagade Han LLP

(57) ABSTRACT

Disclosed herein are devices for altering gaseous flow within a lung to improve the expiration cycle of an individual, particularly individuals having Chronic Obstructive Pulmonary Disease (COPD). More particularly, devices are disclosed to produce collateral openings or channels through the airway wall so that expired air is able to pass directly out of the lung tissue to facilitate both the exchange of oxygen ultimately into the blood and/or to decompress hyper-inflated lungs.

34 Claims, 9 Drawing Sheets

U.S. PATENT DOCUMENTS

| | | |
|---|---|---|
| 4,407,294 A | 10/1983 | Vilkomerson |
| 4,431,006 A | 2/1984 | Trimmer et al. |
| 4,538,618 A | 9/1985 | Rosenberg et al. |
| 4,582,067 A | 4/1986 | Silverstein et al. |
| 4,658,817 A | 4/1987 | Hardy |
| 4,674,498 A | 6/1987 | Stasz |
| 4,682,596 A | 7/1987 | Bales et al. |
| 4,750,902 A | 6/1988 | Wuchinich et al. |
| 4,757,821 A | 7/1988 | Snyder |
| 4,757,822 A | 7/1988 | Di Giuliomaria et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,785,402 A | 11/1988 | Matsuo et al. |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,869,268 A | 9/1989 | Yoon |
| 4,870,953 A | 10/1989 | DonMicheal et al. |
| 4,887,606 A | 12/1989 | Yock et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,924,863 A | 5/1990 | Sterzer |
| 4,936,281 A | 6/1990 | Stasz |
| 4,967,753 A | 11/1990 | Haase et al. |
| 4,977,898 A | 12/1990 | Schwarzschild et al. |
| 5,002,058 A | 3/1991 | Martinelli |
| 5,030,201 A | 7/1991 | Palestrant |
| 5,069,664 A | 12/1991 | Suess et al. |
| 5,081,993 A | 1/1992 | Kitney et al. |
| 5,100,423 A | 3/1992 | Fearnot |
| 5,105,816 A | 4/1992 | Shimura et al. |
| 5,105,817 A | 4/1992 | Uchibori et al. |
| 5,125,926 A | 6/1992 | Rudko et al. |
| 5,127,917 A | 7/1992 | Niederhauser et al. |
| 5,131,394 A | 7/1992 | Gehlbach |
| 5,148,809 A | 9/1992 | Biegeleisen-Knight et al. |
| 5,170,793 A | 12/1992 | Takano et al. |
| 5,190,528 A | 3/1993 | Fonger et al. |
| 5,201,316 A | 4/1993 | Pomeranz et al. |
| 5,209,721 A | 5/1993 | Wilk |
| 5,226,421 A | 7/1993 | Frisbie et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,275,166 A | 1/1994 | Vaitekunas et al. |
| 5,295,484 A | 3/1994 | Marcus et al. |
| 5,299,578 A | 4/1994 | Rotteveel et al. |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,320,106 A | 6/1994 | Tanaka |
| 5,334,183 A | 8/1994 | Wuchinich et al. |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,427,107 A | 6/1995 | Milo et al. |
| 5,435,314 A | 7/1995 | Dias |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,470,308 A | 11/1995 | Edwards et al. |
| 5,474,075 A | 12/1995 | Goldberg et al. |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,520,684 A | 5/1996 | Imran |
| 5,524,630 A | 6/1996 | Crowley |
| 5,527,292 A | 6/1996 | Adams et al. |
| 5,545,195 A | 8/1996 | Lennox et al. |
| 5,554,118 A | 9/1996 | Jang |
| 5,554,152 A | 9/1996 | Aita et al. |
| 5,555,886 A | 9/1996 | Weng et al. |
| 5,564,434 A | 10/1996 | Halperin et al. |
| 5,571,086 A | 11/1996 | Kaplan et al. |
| 5,571,180 A | 11/1996 | Blom |
| 5,573,531 A | 11/1996 | Gregory |
| 5,588,432 A | 12/1996 | Crowley |
| 5,596,989 A | 1/1997 | Morita |
| 5,615,679 A | 4/1997 | Ri et al. |
| 5,630,837 A | 5/1997 | Crowley |
| D380,266 S | 6/1997 | Boatman et al. |
| 5,647,871 A | 7/1997 | Levine et al. |
| 5,658,279 A | 8/1997 | Nardella et al. |
| 5,658,280 A | 8/1997 | Issa |
| 5,672,172 A | 9/1997 | Zupkas |
| 5,678,555 A | 10/1997 | O'Connell |
| 5,704,361 A | 1/1998 | Seward et al. |
| 5,718,701 A | 2/1998 | Shai et al. |
| 5,736,642 A | 4/1998 | Yost et al. |
| 5,752,518 A | 5/1998 | McGee et al. |
| 5,755,769 A | 5/1998 | Richard et al. |
| 5,755,778 A | 5/1998 | Kleshinski |
| 5,759,769 A | 6/1998 | Sia et al. |
| 5,779,642 A | 7/1998 | Nightengale |
| 5,792,119 A | 8/1998 | Marx |
| 5,795,325 A | 8/1998 | Valley et al. |
| 5,810,008 A | 9/1998 | Dekel et al. |
| 5,830,222 A | 11/1998 | Makower |
| 5,840,431 A | 11/1998 | Kall |
| 5,855,597 A | 1/1999 | Jayaraman |
| 5,860,951 A | 1/1999 | Eggers et al. |
| 5,876,345 A | 3/1999 | Eaton et al. |
| 5,885,219 A | 3/1999 | Nightengale |
| 5,916,158 A | 6/1999 | Webster, Jr. |
| 5,921,995 A | 7/1999 | Kleshinski |
| 5,951,567 A | 9/1999 | Javier, Jr. et al. |
| 5,954,649 A | 9/1999 | Chia et al. |
| 5,957,849 A | 9/1999 | Munro |
| 5,957,919 A | 9/1999 | Laufer |
| 5,967,990 A | 10/1999 | Thierman et al. |
| 5,971,980 A | 10/1999 | Sherman |
| 5,984,871 A | 11/1999 | TenHoff et al. |
| 5,993,484 A | 11/1999 | Shmulewitz |
| 6,002,955 A * | 12/1999 | Willems et al. ............ 600/374 |
| 6,003,517 A | 12/1999 | Sheffield et al. |
| 6,004,269 A | 12/1999 | Crowley et al. |
| 6,004,273 A | 12/1999 | Sakamoto et al. |
| 6,004,319 A | 12/1999 | Gobel et al. |
| 6,011,995 A | 1/2000 | Guglielmi et al. |

| | | |
|---|---|---|
| 6,013,033 A | 1/2000 | Berger et al. |
| 6,015,405 A | 1/2000 | Schwartz et al. |
| 6,024,703 A | 2/2000 | Zanelli et al. |
| 6,032,674 A | 3/2000 | Eggers et al. |
| 6,045,511 A | 4/2000 | Ott et al. |
| 6,045,532 A | 4/2000 | Eggers et al. |
| 6,059,731 A | 5/2000 | Seward et al. |
| 6,064,902 A * | 5/2000 | Haissaguerre et al. ........ 600/381 |
| 6,068,638 A | 5/2000 | Makower |
| 6,070,094 A | 5/2000 | Swanson et al. |
| 6,074,349 A | 6/2000 | Crowley |
| 6,080,109 A | 6/2000 | Baker et al. |
| 6,096,053 A | 8/2000 | Bates |
| 6,112,123 A | 8/2000 | Kelleher et al. |
| 6,117,101 A | 9/2000 | Diederich |
| 6,129,726 A | 10/2000 | Edwards et al. |
| 6,143,019 A | 11/2000 | Motamedi et al. |
| 6,159,225 A | 12/2000 | Makower |
| 6,165,127 A | 12/2000 | Crowley |
| 6,174,323 B1 | 1/2001 | Biggs et al. |
| 6,183,444 B1 | 2/2001 | Glines et al. |
| 6,190,353 B1 | 2/2001 | Makower et al. |
| 6,200,313 B1 | 3/2001 | Abe et al. |
| 6,206,831 B1 | 3/2001 | Suorsa et al. |
| 6,235,024 B1 | 5/2001 | Tu |
| 6,241,742 B1 | 6/2001 | Spence et al. |
| 6,245,020 B1 | 6/2001 | Moore et al. |
| 6,258,100 B1 | 7/2001 | Alferness et al. |
| 6,283,951 B1 | 9/2001 | Flaherty et al. |
| 6,283,983 B1 | 9/2001 | Makower et al. |
| 6,287,290 B1 | 9/2001 | Perkins et al. |
| 6,293,951 B1 | 9/2001 | Alferness et al. |
| 6,309,375 B1 | 10/2001 | Glines et al. |
| 6,336,933 B1 | 1/2002 | Parodi |
| 6,394,956 B1 | 5/2002 | Chandrasekaran et al. |
| 6,488,673 B1 | 12/2002 | Laufer et al. |
| 6,490,474 B1 * | 12/2002 | Willis et al. ................. 600/424 |
| 6,514,249 B1 | 2/2003 | Maguire |
| 6,514,290 B1 | 2/2003 | Loomas |
| 6,585,655 B2 * | 7/2003 | Crowley ..................... 600/463 |
| 6,599,311 B1 | 7/2003 | Biggs et al. |
| 6,623,437 B2 | 9/2003 | Hinchliffe et al. |
| 6,629,951 B2 | 10/2003 | Laufer et al. |
| 6,634,363 B1 | 10/2003 | Danek et al. |
| 6,692,494 B1 | 2/2004 | Cooper et al. |
| 6,712,804 B2 * | 3/2004 | Roue et al. ................... 604/500 |
| 6,712,812 B2 | 3/2004 | Roschak |
| 6,749,606 B2 | 6/2004 | Keast et al. |
| 6,770,070 B1 | 8/2004 | Balbierz |
| 6,970,733 B2 * | 11/2005 | Willis et al. ................. 600/424 |
| 6,997,189 B2 | 2/2006 | Biggs et al. |
| 7,022,088 B2 | 4/2006 | Keast et al. |
| 7,175,644 B2 | 2/2007 | Cooper et al. |
| 2001/0007940 A1 | 7/2001 | Hosheng et al. |
| 2002/0022833 A1 | 2/2002 | Maguire et al. |
| 2002/0042564 A1 | 4/2002 | Cooper et al. |
| 2002/0042565 A1 | 4/2002 | Cooper et al. |
| 2002/0111619 A1 | 8/2002 | Keast et al. |
| 2002/0111620 A1 | 8/2002 | Cooper et al. |
| 2002/0128647 A1 | 9/2002 | Roschak |
| 2003/0070676 A1 | 4/2003 | Cooper et al. |
| 2003/0130657 A1 | 7/2003 | Tom et al. |
| 2004/0073155 A1 | 4/2004 | Laufer et al. |
| 2004/0073201 A1 | 4/2004 | Cooper |
| 2004/0211434 A1 | 10/2004 | Loomas et al. |
| 2004/0220556 A1 | 11/2004 | Cooper et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0171527 A1 | 8/2005 | Bhola |
| 2005/0177144 A1 | 8/2005 | Phan et al. |
| 2005/0182475 A1 | 8/2005 | Jen et al. |
| 2005/0192526 A1 | 9/2005 | Biggs et al. |
| 2006/0116749 A1 | 6/2006 | Willink et al. |
| 2006/0135984 A1 | 6/2006 | Kramer et al. |
| 2006/0142672 A1 | 6/2006 | Keast et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2007/0123922 A1 | 5/2007 | Cooper et al. |

FOREIGN PATENT DOCUMENTS

| | | |
|---|---|---|
| EP | 0347098 A2 | 12/1989 |
| EP | 0443256 A1 | 8/1991 |
| JP | 2000-107178 A2 | 4/2000 |
| JP | 2001-104315 A2 | 4/2001 |
| WO | WO 89/06515 A1 | 7/1989 |
| WO | WO 90/01300 A1 | 2/1990 |
| WO | WO 95/02361 | 1/1995 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 | 7/1998 |
| WO | WO 99/01076 A1 | 1/1999 |
| WO | WO 99/11182 A1 | 3/1999 |
| WO | WO 99/25419 A1 | 5/1999 |
| WO | WO 99/60953 | 12/1999 |
| WO | WO 00/67825 | 11/2000 |
| WO | WO 00/72908 | 12/2000 |
| WO | WO 01/32088 | 5/2001 |
| WO | WO 02/00278 | 1/2002 |

* cited by examiner

ELECTROSURGICAL DEVICE HAVING HOLLOW TISSUE CUTTING MEMBER AND TRANSDUCER ASSEMBLY

CROSS REFERENCE TO RELATED APPLICATIONS

This application is a continuation of U.S. patent application Ser. No. 10/079,605, now U.S. Pat. No. 7,022,088, filed Feb. 21, 2002, which is a continuation-in-part of U.S. patent application Ser. No. 09/946,706, now U.S. Pat. No. 6,749,606, filed Sep. 4, 2001, which is a continuation-in-part of U.S. patent application Ser. No. 09/908,087, filed Jul. 18, 2001 and claims the benefit of Provisional Application No. 60/269,130 filed Feb. 14, 2001; U.S. patent application Ser. No. 09/908,087 is a continuation of U.S. patent application Ser. No. 09/633,651, now U.S. Pat. No. 6,692,494, filed Aug. 7, 2000 which claims the benefit of Provisional Application No. 60/176,141 filed Jan. 14, 2000 and Provisional Application No. 60/147,528 filed Aug. 5, 1999, the contents of which are incorporated herein in their entirety.

FIELD OF THE INVENTION

The invention is directed to devices for altering gaseous flow within a lung to improve the expiration cycle of an individual, particularly individuals having Chronic Obstructive Pulmonary Disease (COPD). More particularly, devices are disclosed to produce collateral openings or channels through the airway wall so that expired air is able to pass directly out of the lung tissue to facilitate both the exchange of oxygen ultimately into the blood and/or to decompress hyperinflated lungs. The invention is also directed to medical kits for maintaining collateral openings through airway walls.

BACKGROUND OF THE INVENTION

The term "Chronic Obstructive Pulmonary Disease" (COPD) is generally used to describe the disorders of emphysema and chronic bronchitis. Previously, COPD was also known as Chronic Obstructive Lung Disease (COLD), Chronic Airflow Obstruction (CAO), or Chronic Airflow Limitation (CAL). Some also consider certain types of asthma to fall under the definition of COPD. Emphysema is characterized by an enlargement of air spaces inside the lung. Hence, emphysema is an anatomic definition and it can only be presumed in a living patient. Chronic bronchitis is characterized by excessive mucus production in the bronchial tree. Chronic bronchitis is a clinical definition and denotes those individuals who meet criteria defining the disease. It is not uncommon for an individual to suffer from both disorders.

In 1995, the American Lung Association (ALA) estimated that between 15-16 million Americans suffered from COPD. The ALA estimated that COPD was the fourth-ranking cause of death in the U.S. The ALA estimates that the rates of emphysema is 7.6 per thousand population, and the rate for chronic bronchitis is 55.7 per thousand population.

Those inflicted with COPD face disabilities due to the limited pulmonary functions. Usually, individuals afflicted by COPD also face loss in muscle strength and an inability to perform common daily activities. Often, those patients desiring treatment for COPD seek a physician at a point where the disease is advanced. Since the damage to the lungs is irreversible, there is little hope of recovery. Most times, the physician cannot reverse the effects of the disease but can only offer treatment and advice to halt the progression of the disease.

To understand the detrimental effects of COPD, the working of the lungs requires a cursory discussion. The primary function of the lungs is to permit the exchange of two gasses by removing carbon dioxide from venous blood and replacing it with oxygen. Thus, to facilitate this exchange, the lungs provide a blood gas interface. The oxygen and carbon dioxide move between the gas (air) and blood by diffusion. This diffusion is possible since the blood is delivered to one side of the blood-gas interface via small blood vessels (capillaries). The capillaries are wrapped around numerous air sacs called alveoli which function as the blood-gas interface. A typical human lung contains about 300 million alveoli.

The air is brought to the other side of this blood-gas interface by a natural respiratory airway, hereafter referred to as a natural airway or airway, consisting of branching tubes which become narrower, shorter, and more numerous as they penetrate deeper into the lung. Specifically, the airway begins with the trachea which branches into the left and right bronchi which divide into lobar, then segmental bronchi. Ultimately, the branching continues down to the terminal bronchioles which lead to the alveoli. Plates of cartilage may be found as part of the walls throughout most of the airway from the trachea to the bronchi. The cartilage plates become less prevalent as the airways branch. Eventually, in the last generations of the bronchi, the cartilage plates are found only at the branching points. The bronchi and bronchioles may be distinguished as the bronchi lie proximal to the last plate of cartilage found along the airway, while the bronchiole lies distal to the last plate of cartilage. The bronchioles are the smallest airways that do not contain alveoli. The function of the bronchi and bronchioles is to provide conducting airways that lead inspired air to the gas-blood interface. However, these conducting airways do not take part in gas exchange because they do not contain alveoli. Rather, the gas exchange takes place in the alveoli which are found in the distal most end of the airways.

The mechanics of breathing include the lungs, the rib cage, the diaphragm and abdominal wall. During inspiration, inspiratory muscles contract increasing the volume of the chest cavity. As a result of the expansion of the chest cavity, the pleural pressure, the pressure within the chest cavity, becomes sub-atmospheric with respect to the pressure at the airway openings. Consequently, air flows into the lungs causing the lungs to expand. During unforced expiration, the expiratory muscles relax and the lungs begin to recoil and reduce in size. The lungs recoil because they contain elastic fibers that allow for expansion, as the lungs inflate, and relaxation, as the lungs deflate, with each breath. This characteristic is called elastic recoil. The recoil of the lungs causes alveolar pressure to exceed the pressure at airway openings causing air to flow out of the lungs and deflate the lungs. If the lungs' ability to recoil is damaged, the lungs cannot contract and reduce in size from their inflated state. As a result, the lungs cannot evacuate all of the inspired air.

IN addition to elastic recoil, the lung's elastic fibers also assist in keeping small airways open during the exhalation cycle. This effect is also known as "tethering" of the airways. Such tethering is desirable since small airways do not contain cartilage that would otherwise provide structural rigidity for these airways. Without tethering, and in the absence of structural rigidity, the small airways collapse during exhalation and prevent air from exiting thereby trapping air in within the lung.

Emphysema is characterized by irreversible biochemical destruction of the alveolar walls that contain the elastic fibers, called elastin, described above. The destruction of the alveolar walls results in a dual problem of reduction of elastic recoil and the loss of tethering of the airways. Unfortunately for the individual suffering from emphysema, these two problems combine to result in extreme hyperinflation (air trapping) of the lung and an inability of the person to exhale. In this situation, the individual will be debilitated since the lungs are unable to perform gas exchange at a satisfactory rate.

One further aspect of alveolar wall destruction is that the airflow between neighboring air sacs, known as collateral ventilation or collateral air flow, is markedly increased as when compared to a healthy lung. While alveolar wall destruction decreases resistance to collateral ventilation, the resulting increased collateral ventilation does not benefit the individual since air is still unable to flow into and out of the lungs. Hence, because this trapped air is rich in $CO_2$, it is of little or no benefit to the individual.

Chronic bronchitis is characterized by excessive mucus production in the bronchial tree. Usually there is a general increase in bulk (hypertrophy) of the large bronchi and chronic inflammatory changes in the small airways. Excessive amounts of mucus are found in the airways and semisolid plugs of this mucus may occlude some small bronchi. Also, the small airways are usually narrowed and show inflammatory changes.

Currently, although there is no cure for COPD, treatment includes bronchodilator drugs, and lung reduction surgery. The bronchodilator drugs relax and widen the air passages thereby reducing the residual volume and increasing gas flow permitting more oxygen to enter the lungs. Yet, bronchodilator drugs are only effective for a short period of time and require repeated application. Moreover, the bronchodilator drugs are only effective in a certain percentage of the population of those diagnosed with COPD. In some cases, patients suffering from COPD are given supplemental oxygen to assist in breathing. Unfortunately, aside from the impracticalities of needing to maintain and transport a source of oxygen for everyday activities, the oxygen is only partially functional and does not eliminate the effects of the COPD. Moreover, patients requiring a supplemental source of oxygen are usually never able to return to functioning without the oxygen.

Lung volume reduction surgery is a procedure which removes portions of the lung that are over-inflated. The improvement to the patient occurs as a portion of the lung that remains has relatively better elastic recoil which allows for reduced airway obstruction. The reduced lung volume also improves the efficiency of the respiratory muscles. However, lung reduction surgery is an extremely traumatic procedure which involves opening the chest and thoracic cavity to remove a portion of the lung. As such, the procedure involves an extended recovery period. Hence, the long term benefits of this surgery are sill being evaluated. In any case, it is thought that lung reduction surgery is sought in those cases of emphysema where only a portion of the lung is emphysematous as opposed to the case where the entire lung is emphysematous. In cases where the lung is only partially emphysematous, removal of a portion of emphysematous lung increases the cavity area in which the non-diseased parenchyma may expand and contract. If the entire lung were emphysematous, the parenchyma is less elastic and cannot expand to take advantage of an increased area within the lung cavity.

Both bronchodilator drugs and lung reduction surgery fail to capitalize on the increased collateral ventilation taking place in the diseased lung. There remains a need for a medical procedure that can alleviate some of the problems caused by COPD. There is also a need for a medical procedure that alleviates some of the problems caused by COPD irrespective of whether a portion of the lung, or the entire lung is emphysematous.

The present invention addresses the problems caused by COPD by providing a device configured to create collateral openings through an airway wall which allows expired air to pass directly out of the lung tissue responsible for gas exchange. These collateral openings ultimately decompress hyper-inflated lungs and/or facilitate an exchange of oxygen into the blood.

Furthermore, there is also a need for devices that are able to access remote areas of the body to provide dual functions of locating an acceptable site for removal or cutting of tissue and then removing or cutting the tissue without having to reposition the device. Such a need is evident in dynamically moving environments (e.g., the lungs) where repositioning of a device to find the original target site may be difficult.

Doppler ultrasound is an effective means to determine the presence or absence of a blood vessel within tissue. It is known that sound waves at ultrasonic frequencies travel through tissue and reflect off of objects/interfaces where density gradients exist. In which case, the reflected signal and the transmitted signal will have the same frequency. Alternatively, in the case where the signal is reflected from the blood cells moving through a blood vessel, the reflected signal will have a shift in frequency from the transmitted signal. This shift is known as a Doppler shift. However, since the characteristics of components used to detect Doppler shift vary from characteristics of components used to cut or remove tissue, it is difficult to cut or remove tissue in precisely the same location and immediately after detection has taken place. It is usually required that the component or device used to detect any Doppler shift first must be moved to allow a second component or device to cut or remove the tissue at the same precise location.

For instance, if a device uses energy to create an opening or ablate tissue, the energy delivery components may not have acceptable characteristics to also serve as Doppler components. Furthermore, the process of delivering energy through the device may undesirably impact any Doppler components.

When using Doppler in tissue it is noted that the acoustic impedance of the ultrasound transducer and the acoustic impedance of tissue differ significantly. As a result, the ultrasound signal may experience significant reflection and divergence at the tissue/transducer interface. To address this issue, a tip or lens may be used as an interface between the transducer and tissue.

In common Doppler ultrasound applications, a tip material is selected to provide an optimum acoustic match between the ultrasonic transducer and tissue. This optimum acoustic match is the geometric mean impedance between the tissue and the transducer material, governed by the following equation.

$$Z_{optimum} = (Z_{tissue} \times Z_{transducer})^{1/2}$$

Where $Z_{optimum}$ is the desired acoustic impedance of the tip material; $Z_{tissue}$ is the acoustic impedance of tissue; and $Z_{transducer}$ is the acoustic impedance of the transducer. Generally, $Z_{tissue}$ ranges from 1.38 MRayls (for fat) to 1.70 MRayls (for muscle), while $Z_{transducer}$ is approximately 30 MRayls for ceramic transducer materials. Therefore, using $Z_{transducer}$ of 1.54 MRayls (the average acoustic impedance for tissue) the desirable tip material should have an acoustic impedance around 6.79 MRayls.

Most materials having an acoustic impedance close to this range are made of epoxy composites and range from, for example, 1.78 MRayls for a methylpentene copolymer (e.g., TPX, Matsui Plastics, White Plains, N.Y.) to 4.39 MRayls for high temperature plastics (e.g., CELAZOLE, Curbell Plastics, Glenshaw, Pa.).

One drawback to using Doppler ultrasound devices for placing collateral openings in tissue is that conventional tip materials selected for their desirable acoustic impedance are not effective to deliver energy (e.g., RF, resistive heat, etc.) The acoustic impedance of electrically and thermally conductive materials is higher than the desired acoustic impedance of 6.79 MRayls. For example, $Z_{aluminum}$ is approximately 18 MRayls, $Z_{titanium}$ is approximately 27 MRayls, and $Z_{stainless\ steel}$ is approximately 45 MRayls.

Another drawback to delivering energy through devices configured for Doppler applications is that the transducer is prone to being damaged. For example, when used to deliver therapeutic RF energy, an electrically conductive tip experiences heating. If a sufficient amount of heat is conducted from the tip, the transducer may depolarize. Moreover, conduction of heat through the device may adversely affect the joints and bonds between the transducer, tip and device. As a result, there is the potential of a catastrophic failure of the device if the assembly breaks apart during use in the body.

In view of the above, the present invention provides a device capable of locating an acceptable site for the creation of a collateral opening and then creating an opening in the tissue using a device capable of both functions. While the present invention is discussed as having applicability to creation of collateral openings it was found to have utility for other applications as well. For example, the present invention is suited for the application of energy to tissue in a safe manner (e.g., tumor ablation, tissue removal, application of heat to structures within the body, etc.). Especially when there is a need to avoid blood vessels, or other tissue/organs/structures. The invention has applicability given a need to use of Doppler effect to locate movement within tissue and then apply energy based on the observation of the Doppler effect.

Methods and devices for creating, and maintaining collateral channels are discussed in U.S. patent application Ser. No. 09/633,651, filed on Aug. 7, 2000; U.S. patent application Ser. Nos. 09/947,144, 09/946,706, and 09/947,126 all filed on Sep. 4, 2001; U.S. Provisional Application No. 60/317,338 filed on Sep. 4, 2001, and 60/334,642 filed on Nov. 29, 2001, whereas the entirety of each listed application is incorporated by reference herein.

SUMMARY OF THE INVENTION

The invention related to devices for applying energy to tissue. The invention includes an elongate member having a proximal portion and a distal portion; a transducer assembly and an electrically conductive hollow member located at a distal end of the outer sheath that is coupled to an energy source.

The invention may include a tip having a front and back surface, the back surface being in acoustical communication with the transducer assembly wherein the tip is adapted to communicate a source signal from the transducer assembly out through the front surface, the tip also being adapted to communicate a reflected signal from the front surface to the transducer; and at least two conducting members extending through at least a portion of the elongate member.

The tip of the device functions to direct signals to and from the transducer assembly. The hollow electrically conductive member which cuts or removes tissue via conducting electro-surgical energy (e.g., RF energy) to desired areas. The hollow member can also remove or cut tissue via resistive heating or mechanical cutting.

The invention further includes transducer assemblies wherein the transducer assembly comprises a covering having a proximal and distal end, at least one transducer having at least a first and second pole, a first conductive medium in contact with the first pole of the transducer and extending to at least a portion of an outer surface of the covering, and wherein at least a first of the conducting members is electrically coupled to the first conductive medium, and a second of the conductive members extends through the proximal end of the covering and electrically couples to the second pole of the transducer.

The invention may include insulating layers that serve to protect tissue and/or parts of the device from unwanted heating. The elongate member of the device may also serve as the insulating layer or as additional insulation.

The invention also includes a transducer assembly that is configured to minimize the size of the device so that it may access deeper regions of the body (e.g., deeper regions of airways in the lungs). The transducer assembly may include a covering that is either conductive or is covered by a conductive medium. As such, the covering (or conductive medium) provides an electrical path to a pole of the transducer, thereby eliminating the need for a separate electrical connection.

The invention also includes a medical device for detecting Doppler shift and for applying energy to tissue, the medical device comprising an elongate member having a proximal portion and a distal portion; a transducer means (e.g., a transducer assembly as described herein) for generating a source signal and for receiving a reflected signal wherein the transducer means is located towards the distal portion of the elongate member; a directing means (e.g., a tip as described herein) for directing the source signal and the reflected signal, the directing means located adjacent to and being in acoustical communication with the transducer means, a first conducting member and a second conducting member both extending from the proximal portion of the elongate member to the distal portion of the elongate member, the conducting members electrically coupled to at least the transducer assembly, and an energy-conducting means (e.g., an electrically conductive member) for applying energy to tissue, the energy-conducting means located exterior to the transducer means and the signal directing means.

DETAILED DESCRIPTION OF THE INVENTION

Figure 1A:
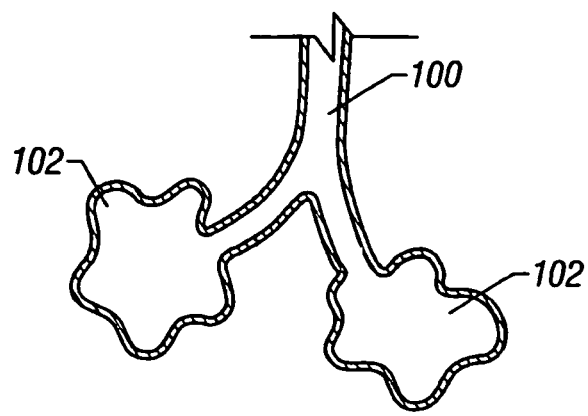
FIGS. 1A-1C illustrate various states of the natural airways and the blood-gas interface.
Figure 1B:
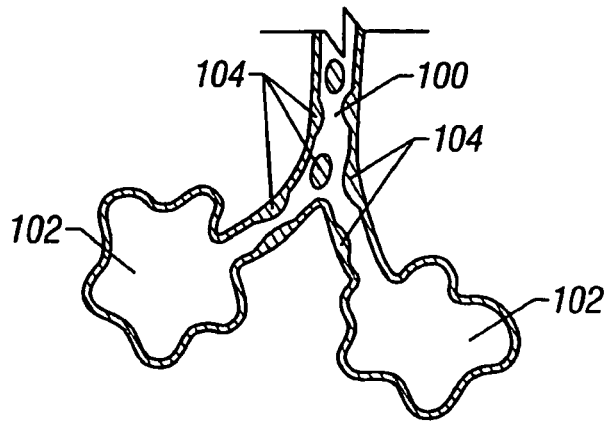
Figure 1C:
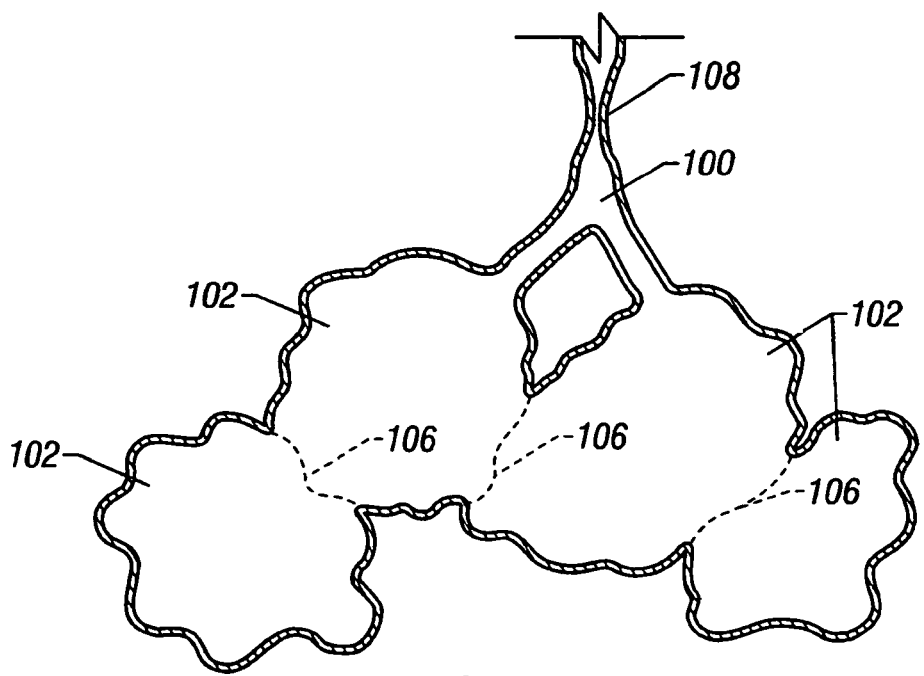

Prior to considering the invention, simplified illustrations of various states of a natural airway and a blood gas interface found at a distal end of those airways are provided in FIGS. 1A-1C. FIG. 1A shows a natural airway 100 which eventually branches to a blood gas interface 102. FIG. 1B illustrates an airway 100 and blood gas interface 102 in an individual having COPD. The obstructions 104 (e.g., excessive mucus resulting from COPD, see above) impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A-1C. More usually, the states of the lung depicted in FIGS. 1B and 1C are often found in the same lung.

The following illustrations are examples of the invention described herein. It is contemplated that combinations of aspects of specific embodiments/variations or combinations of the specific embodiments/variations themselves are within the scope of this disclosure.

As will be explained in greater detail below, the production and maintenance of collateral openings or channels through airway walls permits expired air to pass directly out of the lung tissue and into the airways to ultimately facilitate exchange of oxygen into the blood and/or decompress hyper inflated lungs. The term 'lung tissue' is intended to include the tissue involved with gas exchange, including but not limited to, gas exchange membranes, alveolar walls, parenchyma and/or other such tissue. To accomplish the exchange of oxygen, the collateral channels allow fluid communication between an airway and lung tissue. Therefore, gaseous flow is improved within the lung by altering or redirecting the gaseous flow within the lung, or entirely within the lung.

Figure 1D:
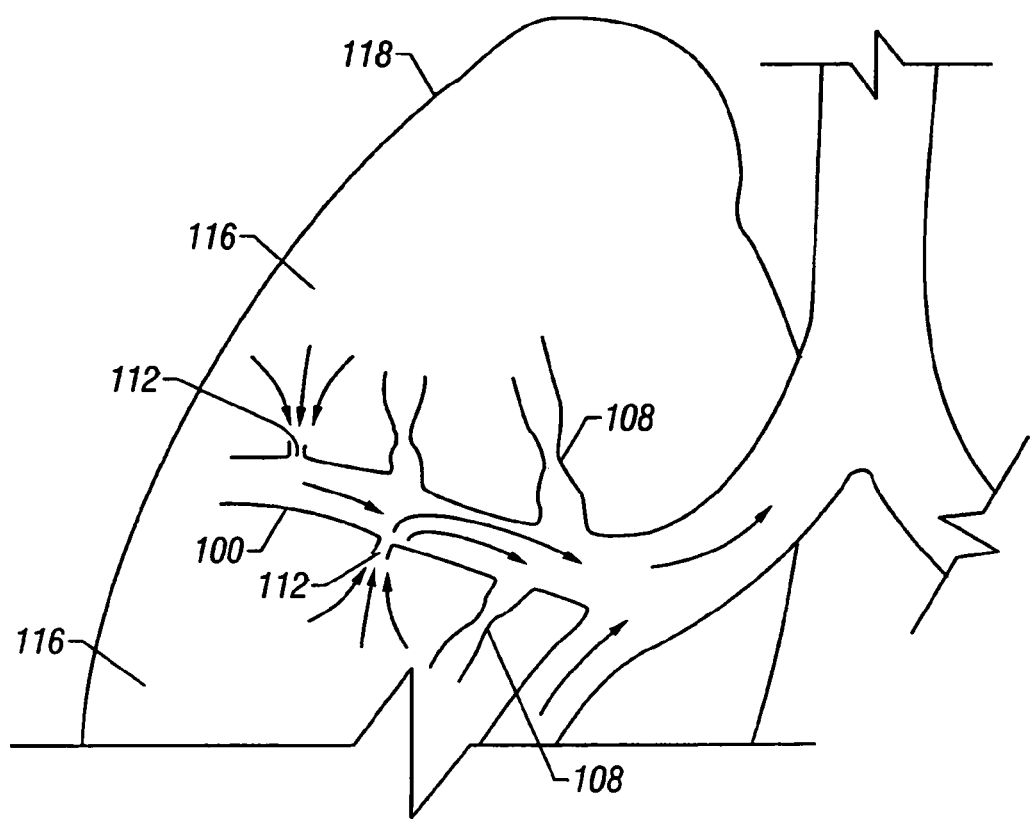
FIG. 1D illustrates a schematic of a lung demonstrating a principle of the effect of collateral channels placed therein.

FIG. 1D illustrates a schematic of a lung 118 to demonstrate a benefit of the production and maintenance of collateral openings or channels through airway walls. As shown, a collateral channel 112 (located in an airway wall 110) places lung tissue 116 in fluid communication with airways 100 allowing expired air to directly pass out of the airways 100. The term channel is intended to include an opening, cut, slit, tear, puncture, or any other conceivable artificially created opening. As shown, constricted airways 108 may ordinarily prevent air from exiting the lung tissue 116. In the example illustrated in FIG. 1D, there is no implanted structure placed in the collateral channel 112. However, conduits (not shown) may be placed in the collateral channels 112 to assist in maintaining the patency of the collateral channels 112. Examples of conduits may be found in the applications discussed above. While there is no limit to the number of collateral channels which may be created, it is preferable that 1 or 2 channels are placed per lobe of the lung. For example, the preferred number of channels is 2-12 channels per individual patient. In current trials, it was found that 1-4 channels placed per lobe of the lung and 4-16 channels per individual patient was preferable. This number may vary on a case by case basis. For instance, in some cases an emphysematous lung may require 3 or more collateral channels in one or more lobes of the lung.

In the following explanation of figures, similar numerals may represent similar features for the different variations of the invention.

The invention herein is described by examples and a desired way of practicing the invention is described. However, the invention as claimed herein is not limited to that specific description in any manner. Equivalence to the description as hereinafter claimed is considered to be within the scope of protection of this patent.

The devices of the present invention are configured to locate a target site for creation of a collateral channel in the tissue and to create an opening in tissue. As discussed above, a benefit of this combination feature is that a single device is able to select a target location and then create an opening without having been moved. Although the device is discussed as being primarily used in the lungs, the device is not limited as such and it is contemplated that the invention has the utility in other areas as well, specifically in applications in which blood vessels or other structures must be avoided while cutting or removing tissue (one such example is tumor removal.)

The present invention includes the use of a device which is able to detect the presence or absence of a blood vessel by placing a front portion of the device in contact with tissue. One variation of the invention includes the use of Doppler ultrasound to detect the presence of blood vessels within tissue. However, the frequency of the signals is not limited to the ultrasonic range, for example the frequency may be within the range of human hearing, etc.

The ultrasound Doppler operates at any frequency in the ultrasound range but preferably between 2 Mhz-30 Mhz. It is generally known that higher frequencies provide better resolution while lower frequencies offer better penetration of tissue. In the present invention, because location of blood vessels does not require actual imaging, there may be a balance obtained between the need for resolution and for penetration of tissue. Accordingly, an intermediate frequency may be used (e.g., around 8 Mhz). A variation of the invention may include inserting a fluid into the airway to provide a medium for the Doppler sensors to couple to the wall of the airway to detect blood vessels. In those cases where fluid is not inserted, the device may use mucus found within the airway to directly couple the sensor to the wall of the airway.

Figure 2A:
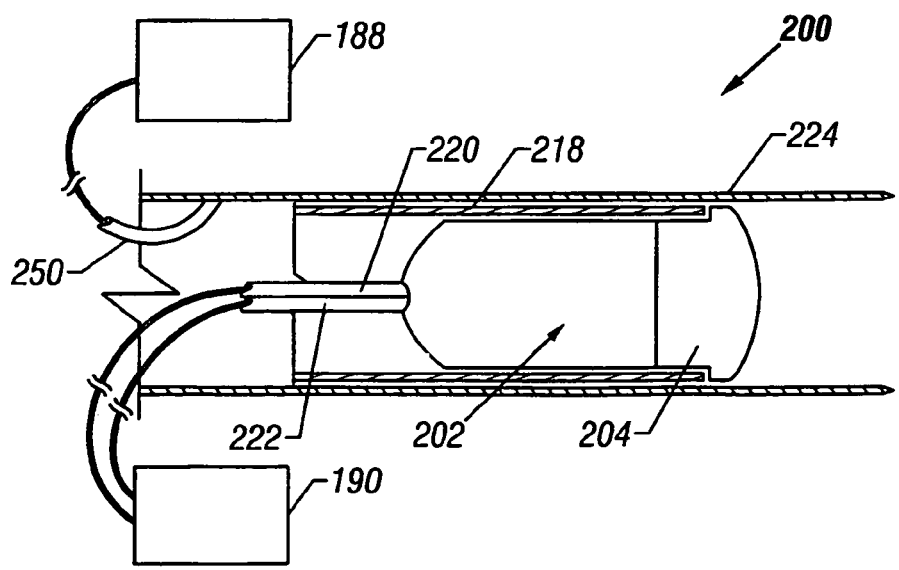
FIG. 2A is a sectional view of a variation of the invention having a conductive member which creates the collateral channel.

FIG. 2A illustrates a sectional side view of a variation of the inventive device 200. The device 200 includes a transducer assembly 202 (variations of which are described in more detail below.) As shown in the figure, a tip 204 is adjacent to the transducer assembly 202. It is contemplated that, throughout this disclosure, the transducer assembly 202 may be a transducer or a transducer coupled with a covering and other components (examples of which are discussed below). Furthermore, the inventive device 200 may be used without a tip 204. A portion of the transducer assembly 202 is located towards a distal portion of an elongate member 218. The transducer assembly of any variation of the present invention may be located within the elongate member, or it may be located within a portion of the tip of the device. In any case, the transducer assembly will be located towards the distal portion of the elongate member. The elongate member described herein may be comprised of any commercially available medical-grade flexible tubing. Furthermore, the elongate member may be selected from material that provide insulation from the heat generated by the device. For example, the elongate member may comprise a PTFE material. In such cases, the elongate member will provide insulation for tissue that is adjacent to the area where creation of a collateral channel is desired. Also, in some cases, insulation may be required to prevent damage to the transducer assembly.

The device 200 further includes a first conducting member 220 and a second conducting member 222 (e.g., wires) both extending through at least a portion of elongate member 218 to the transducer assembly 202. The conducting members 220, 222 may extend through the lumen of the elongate member 218 or may extend in the wall of the elongate member 218. In any case, the conducting members 220, 220 provide the energy and controls 190 for the transducer assembly 202. For example, the conducting members 220, 222 may be coupled to an ultrasound source 190. Moreover, variations of the inventive device include conducting members 220, 222 which may be comprised of a series of wires, with one set of wires being coupled to respective poles of the transducer, and any number of additional sets of wires extending through the device. Ultimately, the wires enable the device to couple to energy and control units. Although not illustrated, the device 200 may also include an outer sheath (not shown in FIG. 2A) in which the device 200 may be advanced to a target tissue site.

In the variation depicted in FIG. 2A, the device 200 includes a hollow electrically-conductive member 224 (e.g., a stainless steel thin walled tubing such as a hypo-tube, cannula tubing such as that used for needles, etc.). The hollow electrically-conductive member 224 is coupled to an energy source 188 (e.g., a monopolar or bi-polar RF energy source.) Accordingly, the hollow electrically-conductive member 224 may be used to remove or cut tissue (e.g., to create a collateral channel) once the ultrasound assembly 202 is used to find an acceptable location for placement of the collateral channel. The hollow electrically-conductive member 224 may be coupled to the energy source 188 via a third conductive member 250. Alternatively, the hollow electrically-conductive member 224 may be coupled to the energy source 188 via other means (e.g., use of one of the conducting members coupled to the transducer assembly.) It should be noted that the hollow electrically-conductive member 224 may be insulated such that only a distal portion of the member 224 is enabled to create a collateral channel. Such a configuration may be better direct heat or current (i.e., if used as an RF device) to the desired location.

In the variation depicted in FIG. 2A, the transducer assembly 202 and elongate member 218 may be slidably located in the hollow electrically-conductive member 224. Therefore, when the conductive member 224 is used to create a collateral channel, it may be desirable to space the transducer assembly 202 a sufficient distance from the conductive member 224 to prevent damage to the assembly 202. The degree of spacing will depend upon the duration and amount of energy applied. The sliding actuation of the device may be automated or manual. In a simple variation, one member may be slidable to another via use of a knob that permits relative movement between the components. Furthermore, it may be desirable to allow the operator of the device to actuate the components with a single hand.

Figure 2B:
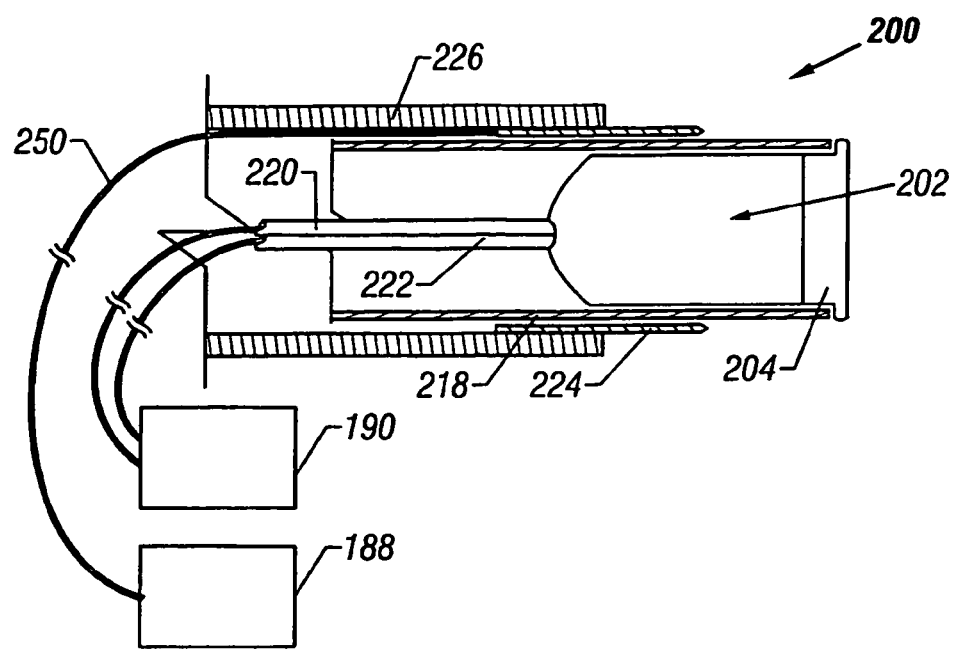
FIG. 2B is a sectional view of another variation of the invention having a conductive member.

FIG. 2B illustrates another variation of a device 200 for creating collateral channels. In this variation, a transducer assembly 202 is provided with a tip 204. It should be noted that the shape of the tips illustrated in the figures is not meant to be limiting. Rather, the tip shapes shown are for illustration purposes only. The tip 204 is located adjacent to the transducer assembly 202. A portion of the transducer assembly 202 may be located towards a distal portion of an elongate member 218. As stated above, the transducer assembly of any variation of the present invention may be located within the elongate member, or it may be located within a portion of the tip of the device. In the variation depicted in FIG. 2B the device 200 also includes an (optional) outer sheath 226. As illustrated, the device includes a hollow electrically-conductive member 224 coupled to an energy source 188 using a third conducting member 250.

Figure 2C:
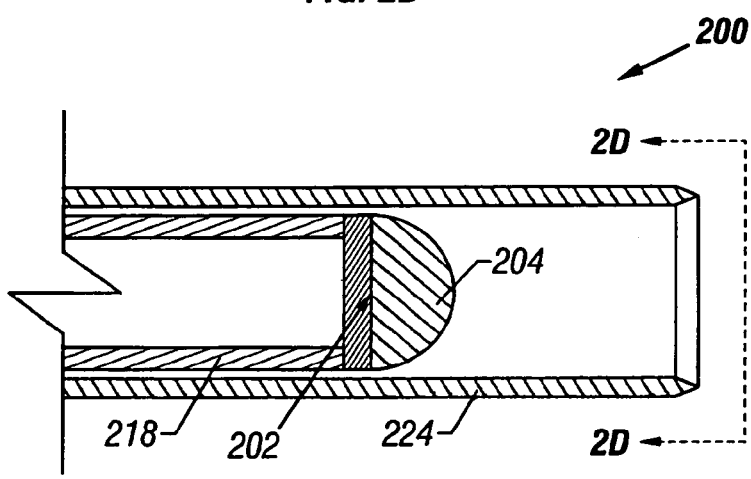
FIGS. 2C-2D illustrate another variation of the invention.
Figure 2D:
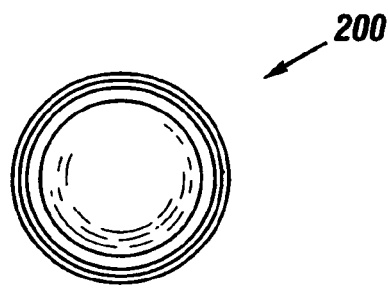

FIG. 2C illustrates another variation of the invention device 200 where a hollow electrically-conductive member 224 is exterior to a transducer assembly 202. In this variation, the transducer assembly 202 comprises a transducer. The hollow electrically-conductive member 224 may be either an RF device or a resistive heating device. Alternatively, the hollow members 224 of the present invention may be mechanical devices that simply cut the tissue. For example, the hollow electrically-conductive member 224 can be a hypo-tube placed over the transducer assembly 202. In this variation of the device 200, the transducer assembly 202 may be moveable within the hollow electrically-conductive member 224, or the hollow electrically-conductive member 224 may be moveable over the transducer assembly 202. In either case, the transducer assembly 202 may be advanced out of hollow electrically-conductive member 224 to determine the presence of a blood vessel. If no blood vessel is found, the transducer assembly 202 may be withdrawn into the hollow electrically-conductive member 224 allowing it to cut or remove tissue. FIG. 2D illustrates a view taken along the line 2D in FIG. 2C.

Although FIGS. 2A-2C illustrate the inventive device 200 as having a transducer assembly 202 and tip 204 that are slidable relative to the conductive member 224, it is noted that the conductive member 224 may be fixed relative to the tip 204 or the transducer assembly 202. In such a case, the conductive member 224 will be fixed such that the tip 204 of the device 200 is able to contact tissue while the conductive member 224 is either slightly behind the front surface of the tip 204 or the conductive member 224 is already engaging the tissue. After determining that energy may be applied, the entire device 200 with the fixed conductive member 224 may be advanced to permit the conductive member 224 to remove tissue.

Although the transducer assembly is adapted to generate a source signal and receive a reflected signal, variations of the invention may omit the transducer covering and other structures not necessary to generate a source signal and receive a reflected signal. Therefore, it is contemplated that the invention may simply have a transducer that is coupled to a controller.

As discussed herein, for some variations of the invention it is desirable to minimize the size of the device especially at the distal end. Although the invention may be any size, it was found that an overall device diameter of 0.071" was acceptable. As noted, because the device is advanced through the airways, the device may treat deeper areas in the airways of the lungs given a smaller outside diameter of the distal end of the device. This size also permits delivery of the device into the lungs through the working channel of a standard bronchoscope or endoscope. However, this reduction in size is limited as functionality of the device may suffer. For example, one or more wires will be selected such that they will deliver sufficient RF energy over a desired period of time without experiencing unacceptable heating. Therefore, the smallest acceptable cross sectional area of a single wire or multiple wires will be a balance of the energy delivery requirements of the device versus the characteristics of the wire or wires.

Figure 3A:
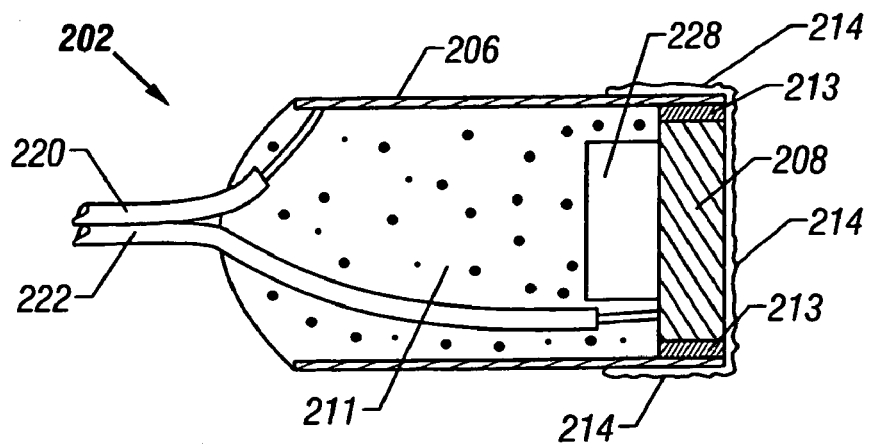
FIGS. 3A-3B illustrate cross sectional views of examples of transducer assemblies of the present invention.
Figure 3B:
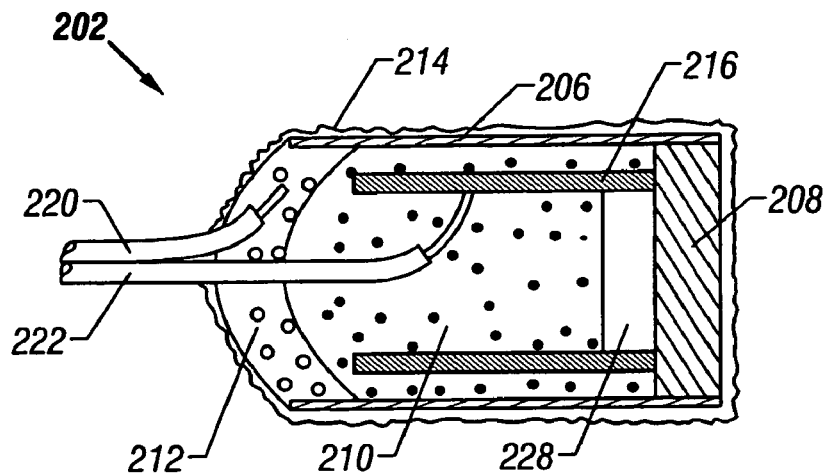

FIGS. 3A-3B illustrate variations of the transducer assembly 202 which are configured to reduce an overall size of the assembly. FIG. 3A illustrates a cross-sectional view of a basic variation of a transducer assembly 202 for use with the present invention. For illustration purposes, the transducer assembly 202 illustrated in FIG. 3A is shown without a tip. The transducer assembly 202 includes at least one transducer 208 (e.g., a piezoelectric transducer.) In this variation, the front surface of the transducer 208 comprises a first pole and the rear surface comprises a second pole.

The transducer or transducers may comprise a piezo-ceramic crystal (e.g., a Motorola PZT 3203 HD ceramic). In the current invention, a single-crystal piezo (SCP) is preferred, but the invention does not exclude the use of other types of ferroelectric material such as poly-crystalline ceramic piezos, polymer piezos, or polymer composites. The substrate, typically made from piezoelectric single crystals (SCP) or ceramics such as PZT, PLZT, PMN, PMN-PT; also, the crystal may be a mutli layer composite of a ceramic piezoelectric material. Piezoelectric polymers such as PVDF may also be used. Micromachined trandsducers, such as those constructed on the surface of a silicon wafer are also contemplated (e.g., such as those provided by Sensant of San Leandro, Calif.) As described herein, the transducer or transducers used may be ceramic pieces coated with a conductive coating, such as gold. Other conductive coatings include sputtered metal, metals, or alloys, such as a member of the Platinum Group of the Periodic Table (Ru, Rh, Pd, Re, Os, Ir, and Pt) or gold. Titanium (Ti) is also especially suitable. The transducer may be further coated with a biocompatible layer such as Parylene or Parylene C.

The covering 206 of the transducer assembly 202 may contain at least a portion of the transducer 208. In some variations of the invention, the covering 206 may comprise a conductive material. In such cases the covering 206 itself becomes part of the electrical path to the first pole of the transducer 208. Use of a conductive covering 206 may require insulating material 213 between the sides of the transducer 208, thereby permitting a first conductive medium 214 to electrically couple only one pole of the transducer 208 to the covering 206.

At least a portion of the front surface of the transducer 208, will be in contact with the conductive medium 214. The conductive medium 214 permits one of the poles of the transducer 208 to be placed in communication with a conducting member that is ultimately coupled to a power supply. As shown in this example, the conductive medium 214 places the pole of the transducer 208 in electrical communication with the covering 206. In some variations the conductive medium 214 may coat the entire transducer 208 and covering 206. Alternatively, the conductive medium 214 may be placed over an area small enough to allow for an electrical path between a conducting member and the respective pole of the transducer 208. The conductive medium 214 may be any conductive material (e.g., gold, silver, tantalum, copper, chrome, or any bio-compatible conductive material, etc. The material may be coated, deposited, plated, painted, wound, wrapped (e.g., a conductive foil), etc. onto the transducer assembly 202.

The transducer assembly 202 depicted in FIG. 3A also illustrates conducting members 220, 222 electrically coupled to respective poles of the transducer 208. Optionally, the conducting members 220, 222 may be encapsulated within an epoxy 211 located within the covering 206. The epoxy 211 may extend to the transducer 208 thereby assisting in rotating both the conducting members 220, 222 and transducer 208 within the covering. It may also be desirable to maintain a gap 228 between the transducer 208 and any other structure. It is believed that this gap 228 improves the ability of the transducer assembly 202 to generate a signal.

FIG. 3B illustrates another variation of a transducer assembly 202. In this variation, the conductive medium 214 extends over the entire transducer covering 206. Accordingly, the covering 206 may be made of a non-conducting material (e.g., a polyamide tube, polyetherimide, polycarbonate, etc.) The transducer assembly 202 may further comprise a second tube 216 within the covering 206. This second tube 216 may be a hypo-tube and may optionally be used to electrically couple one of the conducting members to a pole of the transducer 208. As shown, the covering 206 may contain a non-conductive epoxy 210 (e.g., Hysol 2039/3561 with Scotchlite glass microspheres B23/500) which secures both the conducting member and the second tube 216 within the covering 206. This construction may have the further effect of structurally securing the transducer 208 within the assembly 202. Again, a gap 228 may or may not be adjacent to the transducer to permit displacement of the transducer 208.

FIG. 3B also illustrates the assembly 202 as having a conductive epoxy 212 which encapsulates the alternate conducting member 220. An example of a conductive epoxy is Bisphenol epoxy resin with silver particulates to enable conductivity. The particulates may be from 70-90% of the resin composition. The resin may then be combined with a hardener (e.g., 100 parts per resin per 6 parts hardener.) The conductive epoxy 212 is in electrical communication with the conductive medium 214 allowing for a conductive path from the conducting member 220 to the conductive medium 214. Accordingly, use of the conductive epoxy 212 secures the conducting member 220 to the assembly 202 while electrically coupling the conducting member 220 to the transducer via the conductive coating 214.

Although the transducer assembly is adapted to generate a source signal and receive a reflected signal, variations of the invention may omit the transducer covering and other structures not necessary to generate a source signal and receive a reflected signal. Therefore, it is contemplated that the invention may simply have a transducer that is coupled to a controller.

FIGS. 4A-4D, illustrate possible variations of the tip 204 of the transducer assembly. It is noted that these variations are provided for illustrative purposes and are not meant to be exhaustive. The tips 204 of the present invention may function as a lens to disperse and/or direct a signal over a substantial portion of the outer surface of the tip 204. The tip 204 also is adapted to disperse and/or direct (e.g., by diffraction) a reflected signal towards the transducer (not shown in FIGS. 4A-4D). Accordingly, given the above described configuration, the inventive device 200 will be able to detect vessels with substantially most of the tip 204. The tip may comprise a signal directing means.

The tip 204 is designed such that it interfere and redirects the signals in a desired direction in a manner like a lens. It also may be desirable to place an epoxy between the tip 204 and the transducer. Preferably, the epoxy is thin and applied without air gaps, bubbles or pockets. Also, the density/hardness of the epoxy should provide for transmission of the signal while minimizing any effect or change to the source signal. The configuration of the transducer assembly 202 permits the tip 204 to disperse a signal over a substantial portion of its outer surface 240. The tip 204 also is adapted to refract a reflected signal towards the transducer 208. Accordingly, given the above described configuration, the inventive device will be able to detect vessels with any part or substantially all of the lens 204 that contacts tissue.

Although the tip is of the present invention is able to transmit a source signal and receive a reflected signal, the invention is not limited to requiring both functions. For example, the inventive device could be configured to generate a source signal and direct the source signal to an area of interest but a second device or transducer assembly could be used to receive the reflected signal. Accordingly, a separate device could be used to generate the source signal with the inventive device being used to receive the reflected signal.

The tip 204 may be comprised of materials such as a dimethyl pentene, a methylpentene copolymer (plastic-TPX), aluminum, carbon aerogel, polycarbonate (e.g., Lexan), polystyrene, or etc., any standard material used for ultrasound applications.

Figure 4A:
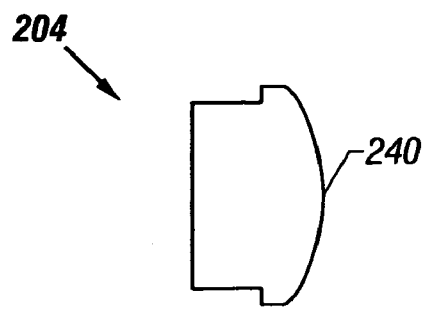
FIGS. 4A-4D illustrate examples of tip configuration of the present invention.
Figure 4B:
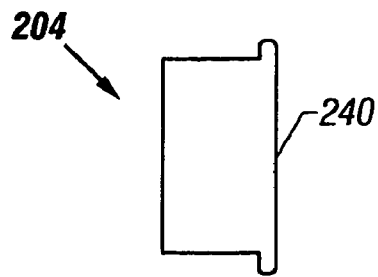
Figure 4C:
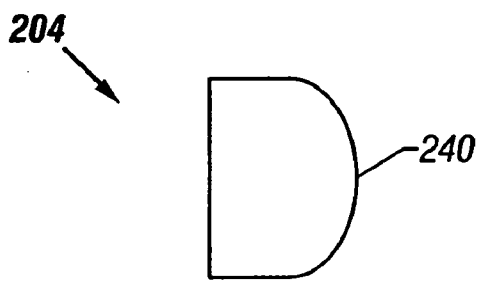
Figure 4D:
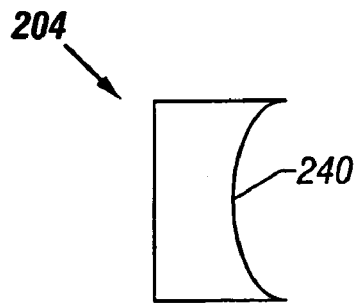

As illustrated in FIG. 4A, although the front surface 240 of the tip 202 is illustrated as being hemispherical, the tip 204 may have other profiles as well. For example, it is desirable that the tip 204 produce a certain amount of divergence of the signal being passed therethrough. However, depending on a variety of factors (e.g., material, frequency of the signal, etc.) a tip 204 may encounter excessive divergence which is destructive to the outgoing signal. Accordingly, it may be desirable to produce a tip 204 as illustrated in FIG. 4B in which a front surface 240 of the tip 204 is substantially flat. The degree of flatness of the tip 204 will often depend upon experimentation to reduce the amount of destructive reflections, thus minimizing excessive divergence due to differences in speed of sound in tip versus tissue. For example, when using a tip that is conductive to an ultrasound signal (e.g., TPX) a rounded tip can be used since there is not excessive divergence of the source signal. Use of a material that is not as conducive to ultrasound require a flatter tip due to the resulting divergence of the source signal. FIG. 4C illustrates another variation of a tip 204 having a rounded front surface 240 but with no projections on the sides of the tip 204. FIG. 4D illustrates a tip 204 with a concave front surface 240.

It may also be desirable that the device is configured such that there are no exposed sharp edges that may cause any unintended damage to tissue while the device is being used to determine the presence or absence of a blood vessel. In such a case, for example, the tip may be designed such that it doesn't have sharp edges, or any sharp edges may be covered by other parts of the device (e.g., the elongate member, an outlet sheath, etc.)

FIGS. 5A-5E illustrate examples of configurations for redundant joints to retain the tip 204 with the device by increasing the retention strength of the tip 204 within the device. It is contemplated that these concepts may be combined as necessary with the variations of the invention disclosed herein.

Figure 5A:
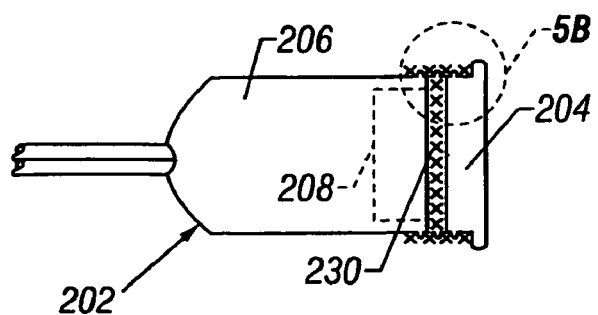
FIGS. 5A-5E illustrate various configurations to retain a tip to devices of the present invention.
Figure 5B:
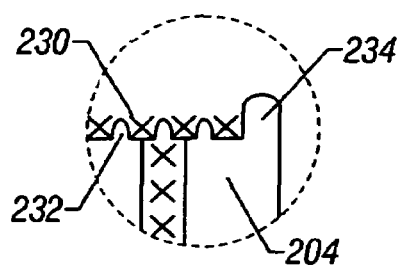

FIG. 5A illustrates a tip 204 attached the transducer assembly 202. The tip 204 may be bonded, via a retaining epoxy 230, to either the transducer 208 or to the first conducive medium, such as a gold coating, etc. (not shown). Naturally, the retaining epoxy 230 should be selected to minimize any interference to the source or return signal. Examples of the retaining epoxy 230 include Epotech 301, Epotech 353, Epotech 377, provided by Epoxy Technology, Inc., Bellerica, Mass. As illustrated in FIG. 5A, the retaining epoxy 230 may run along the sides of the transducer assembly 202 in which case the epoxy 230 may adhere to the elongate member (not shown). Moreover, the tip 204 may be machined, etched, etc., to contain a plurality of small grooves 232 for seating the retaining epoxy 230. Such a configuration increases the retention strength of the tip 204 within the device and is shown in FIG. 5B which illustrates a magnified view of the section marked 5B found in FIG. 5A. Although not shown, the epoxy 230 may be placed on a lip 234 of the lens 204. In such cases, the epoxy 230 may also adhere to a front end of the elongate member (not shown.)

Figure 5C:
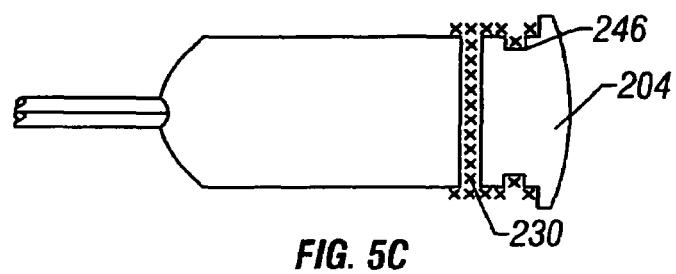

FIG. 5C illustrates another variation where the tip 204 has a single groove 246 for better retention of the tip 204 in the device. It is noted that the grooves discussed herein may either extend around the entire perimeter of the tip 204 or they may extend over only portions of the tip 204. In the latter case, the term 'groove' is intended to include structures such as: dimples, furrows, indentations, pockets, notches, recesses, voids, etc. For sake of illustration, the elongate member is not illustrated in these figures.

Figure 5D:
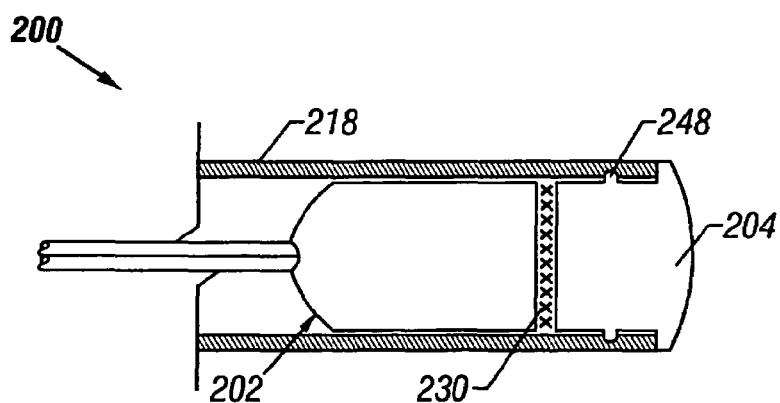

FIG. 5D illustrates a variation of a tip 204 having at least one rib 248 which may provide a friction fit with the elongate member 218. The rib 248 may be deformable or rigid.

Figure 5E:
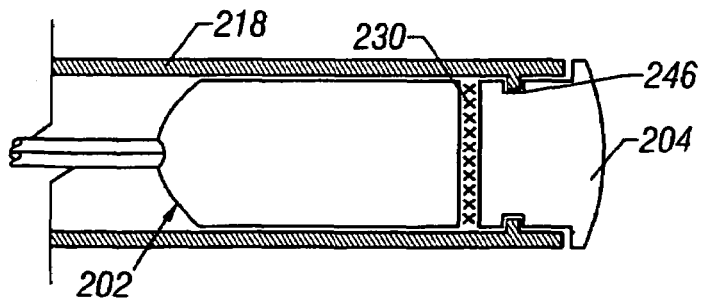

FIG. 5E illustrates another variation of the invention where the tip has a at least one groove 246 where the elongate member 218 is either crimped or filled into the groove 246.

Figure 6A:
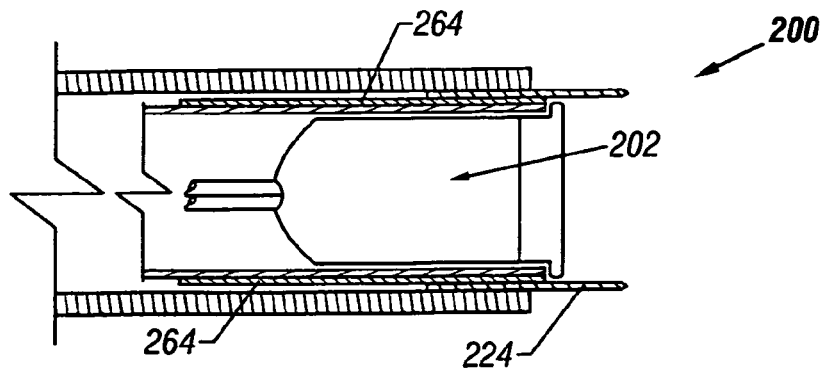
FIGS. 6A-6B illustrate insulating layers on the device.

FIG. 6A illustrates a variation of the device 200 with an insulating layer 264 on the distal end of the device 200. The insulating layer 264 may be a coating, sleeve, etc. which prevents heat generated by the hollow electrically conductive member 224 from adversely affecting either tissue or the transducer assembly 202. The insulating layer 264 may extend over a limited area of the device as needed. Examples of the insulating layer 264 materials include polyimide, silicone, PTFE, FEP, PFA.

Figure 6B:
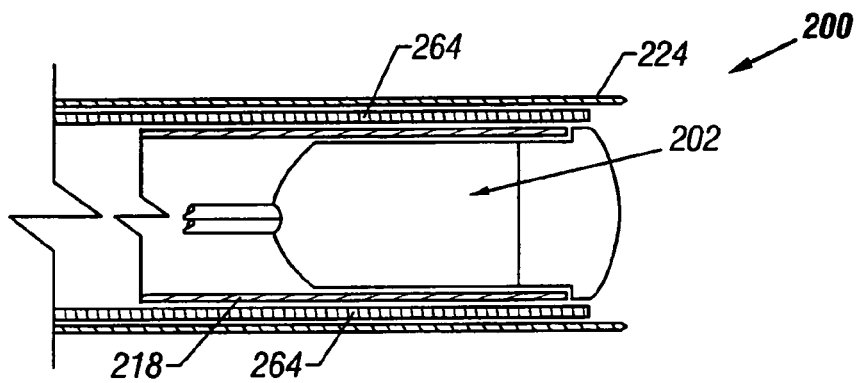

FIG. 6B shows a variation of the device 200 having a hollow conductive member 224. Optionally, an insulating layer 264 may be placed between the conductive member 224 and the transducer assembly 202. It is noted that, as discussed above, the elongate member 218 itself may serve as an insulating member.

Figure 7A:
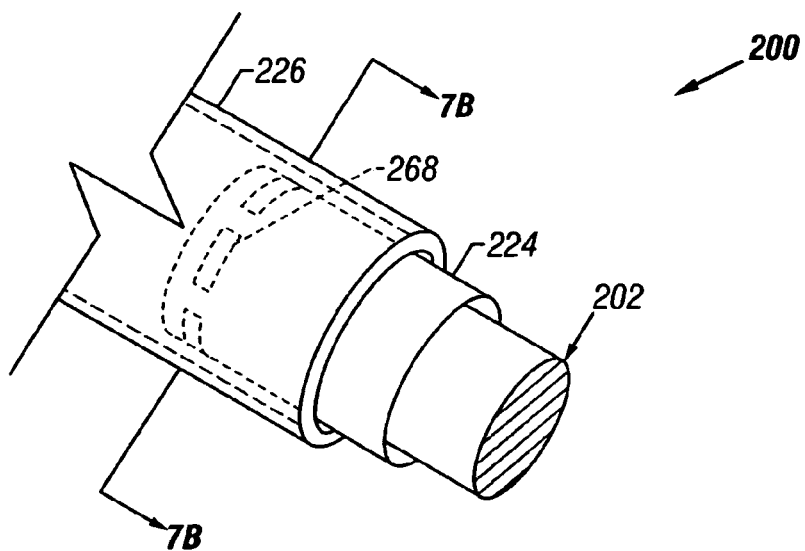
FIG. 7A illustrates a variation of the device where the outer sheath is used to create a redundant joint to retain a hollow electrically-conductive member on the device.
Figure 7B:
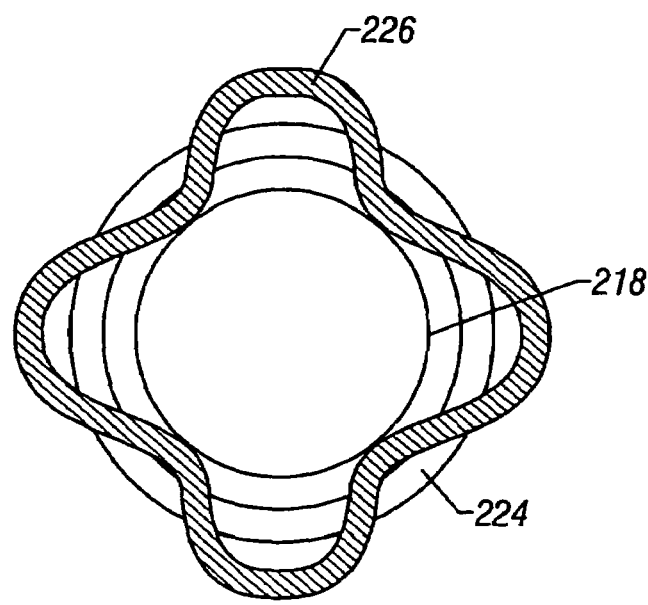
FIG. 7B is a cross sectional view taken along the line 7B-7B of FIG. 7A.

FIG. 7A illustrates a variation of the inventive device 200 having a hollow conductive member 224 with at least one slot 268 (e.g., any opening). The slot 268 enables portions of the sheath 226 to be inserted or formed through the slots 268 thereby providing a structure to retain the conductive member 224 in the device. FIG. 7B shows a cross sectional view taken along the line 7B-7B of FIG. 7A. Obviously, the sheath 226 will be placed inside the slot 268 such that it does not interfere with the transducer assembly 202 or elongate member 218. It is contemplated that epoxy may also be used in conjunction with this configuration.

Figure 8A:
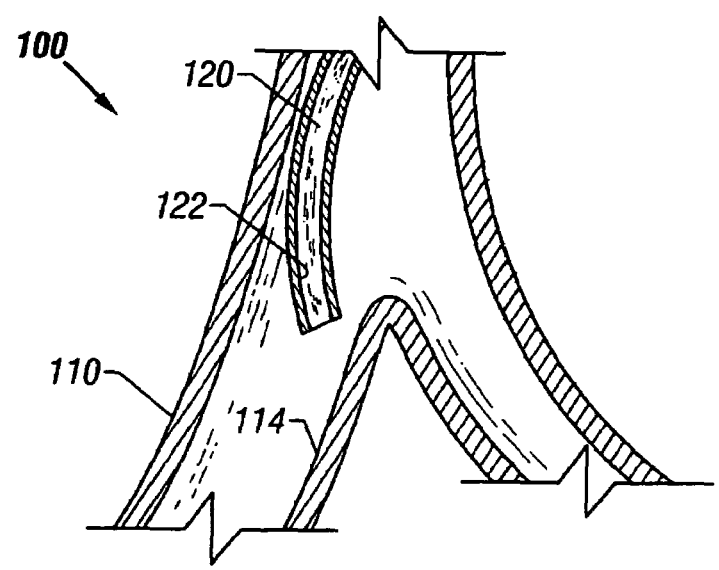
FIG. 8A-8C shows the device when used to create a collateral channel in the airways of the lung.
Figure 8B:
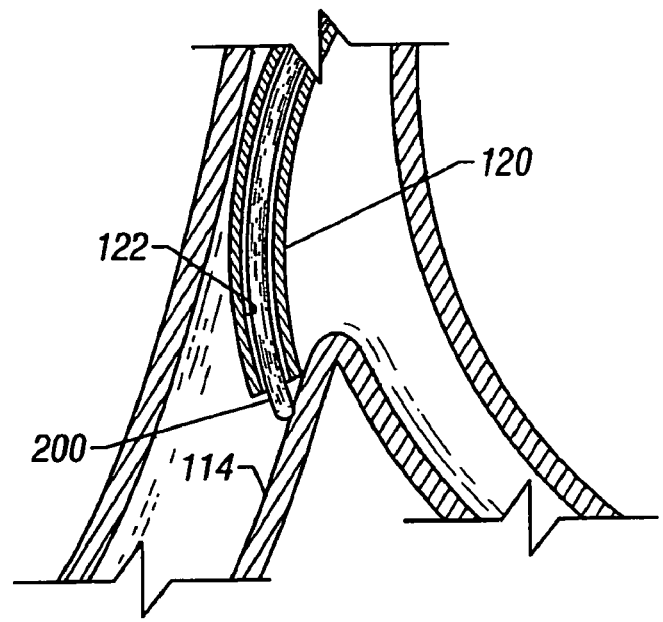
Figure 8C:
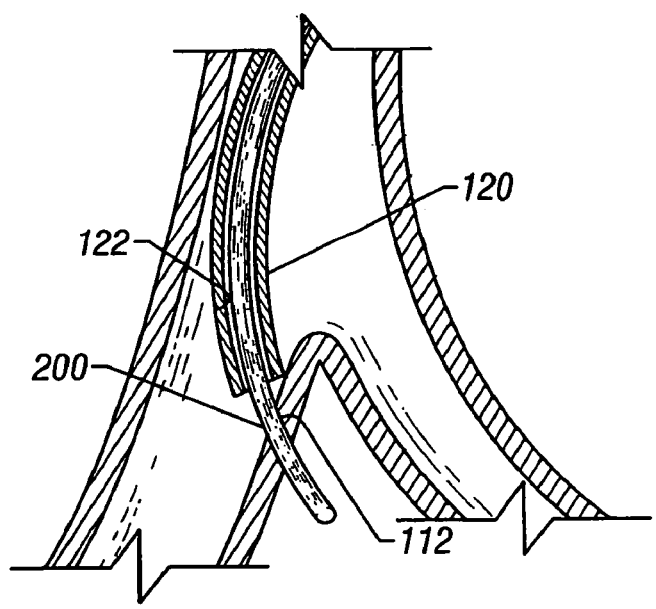

FIGS. 8A-8C illustrates use of the device within a lung to create a collateral channel in the airway wall tissue. FIG. 8A illustrates the advancement of an access device 120 into the airways 100 of a lung. The access device may be a bronchoscope, endoscope, endotracheal tube with or without vision capability, or any type of delivery device. The access device 120 will have at least one lumen or working channel 122. The access device 120 will locate an approximate site 114 for creation of a collateral channel. In cases where the access device 120 is a bronchoscope or similar device, the access device 120 is equipped so that the surgeon may observe the site for creation of the collateral channel. In some cases it may be desirable for non-invasive imaging of the procedure. In such cases, the access device 120 as well as the other devices discussed herein, may be configured for detection by the particular non-invasive imaging technique such as fluoroscopy, "real-time" computed tomography scanning, or other technique being used.

FIG. 8B illustrates a variation of the inventive device 200 advanced through the channel 122 of the access device 120 towards the site 114. The site 114 is then inspected to determine whether a blood vessel is adjacent to the site.

FIG. 8C illustrates the creation of a collateral channel 112. As shown in FIG. 8C, the device 200 may be manipulated to a position that is optimal for creation of the collateral channel 112. It is noted that either the access device 120 or the inventive device 200 may be steerable. Such a feature may assist in the positioning of any of the devices used in the inventive method. Although it is not illustrated, as discussed herein, it is desirable to create the collateral channel such that it is in fluid communication with an air-sac. The fluid communication allows for the release of trapped gasses from the hyper-inflated lung.

The inventive device is configured to communicate with an analyzing device or control unit 190 adapted to recognize the reflected signal or measure the Doppler shift between the signals. As mentioned above, the source signal may be reflected by changes in density between tissue. In such a case, the reflected signal will have the same frequency as the transmitted signal. When the source signal is reflected from blood moving within a vessel, the reflected signal has a different frequency than that of the source signal. This Doppler effect permits determination of the presence or absence of a blood vessel within tissue. The device may include a user interface which allows the user to determine the presence or absence of a blood vessel at the target site. Typically, the user interface provides an audible confirmation signal. However, the confirmation signal may be manifested in a variety of ways (e.g., light, graphically via a monitor/computer, etc.)

Although depicted as being external to the device 200, it is contemplated that the analyzing device 190 may alternatively be incorporated into the device 200. The transducer assembly of the invention is intended to include any transducer assembly that allows for the observation of Doppler effect, e.g., ultrasound, light, sound etc.

It should be noted that the invention includes kits containing the inventive device with any one or more of the following components, an RF energy supply, a Doppler ultrasound controller, a conduit as described in one or more of the applications listed above, and a bronchoscope/endoscope.

We claim:

1. A medical device for applying energy to tissue, the medical device comprising:
    a flexible elongate member having a proximal portion and a distal portion;
    a transducer assembly comprising a transducer having first and second poles;
    wherein said transducer assembly is located towards a distal end of said elongate member distal portion;
    two conducting members extending through at least a portion of said elongate member and in electrical contact with the first and second poles respectively;
    a hollow member located at the distal end of said elongate member, the hollow member adapted to mechanically cut tissue and wherein said hollow member is coupled to an RF energy source via one of the conducting members,
    a tip having a rounded surface configured to avoid damage to tissue and located at a distal end of said elongate member distal portion and having a front and back surface, said back surface being in acoustical communication with said transducer such that said tip is adapted to communicate a source signal from said transducer out through said front surface, said tip also being adapted to communicate a reflected signal from said front surface to said transducer assembly; and
    wherein the transducer assembly is configured to be distally moveable to a distal end of the hollow member.

2. The medical device of claim 1, where the hollow member is moveable over the transducer assembly.

3. The medical device of claim 1, wherein the transducer assembly is advanceable out of the hollow member.

4. The medical device of claim 1, wherein said top comprises a methylpentene copolymer.

5. The medical device of claim 1, further comprising a retaining epoxy placed adjacent to said tip to assist in retaining said top to the device.

6. The medical device of claim 5, wherein a surface of said tip adjacent to said elongate member contains at least one groove, wherein said retaining epoxy fills said groove to increase retention of said tip.

7. The medical device of claim 5, wherein said retaining epoxy is located at least between said tip and said transducer.

8. The medical device of claim 1, wherein said elongate member comprises an insulating member.

9. The medical device of claim 1, further comprising an insulating layer over a portion of said elongate member.

10. The medical device of claim 1, wherein said hollow member comprises a material selected from the group consisting of stainless steel, titanium, and aluminum.

11. The medical device of claim 1, wherein said first and second conducting members are electrically coupled to a control unit to measure the Doppler shift between the transmitted and received signals.

12. The medical device of claim 1, wherein said transducer is a piezo-electric ultrasound transducer.

13. The medical device of claim 1, further comprising a covering surrounding said transducer assembly and wherein said covering comprises a first tube.

14. The medical device of claim 13, wherein said first tube is conductive.

15. The medical device of claim 13, wherein said transducer assembly further comprises a second tube placed within said covering and having an end placed adjacent to said transducer.

16. The medical device of claim 15, wherein said second tube is conductive and where said second conducting member is electrically coupled to said second tube.

17. A medical device for applying energy to tissue, the medical device comprising:
    a flexible elongate member having a proximal portion and a distal portion;
    a transducer assembly comprising a transducer having first and second poles;
    wherein said transducer assembly is located towards a distal end of said elongate member distal portion;
    a conducting member extending through at least a portion of said elongate member and in electrical contact with at least one of the first and second poles;
    a hollow member located at the distal end of said elongate member, the hollow member adapted to mechanically cut tissue and wherein said hollow member is coupled to an energy source via the conducting member,
    a rounded tip configured to avoid damage to tissue and located at a distal end of said elongate member distal portion and having a front and back surface, said back surface being in acoustical communication with said transducer such that said tip is adapted to communicate a source signal from said transducer out through said front surface, said tip also being adapted to communicate a reflected signal from said front surface to said transducer assembly; and
    wherein the transducer assembly is configured to be proximally moveable from a location at least partially distal to a distal end of the hollow member to a position wholly proximal to the distal end of the hollow member.

18. A medical device for applying energy to tissue, the medical device comprising:
- a flexible elongate member having a proximal portion and a distal portion;
- a transducer assembly comprising a transducer having first and second poles;
- wherein said transducer assembly is located towards a distal end of said elongate member distal portion;
- two conducting members extending through at least a portion of said elongate member and in electrical contact with the first and second poles respectively;
- a hollow conductive member located at the distal end of said elongate member, the hollow member adapted to mechanically cut tissue and wherein said hollow conductive member is coupled to an energy source via one of the conducting members;
- a rounded tip configured to avoid damage to tissue and located at a distal end of said elongate member distal portion and having a front and back surface, said back surface being in acoustical communication with said transducer such that said tip is adapted to communicate a source signal from said transducer out through said front surface, said tip also being adapted to communicate a reflected signal from said front surface to said transducer assembly; and
- wherein the transducer assembly is configured to be distally moveable to a distal end of the hollow member.

19. The medical device of claim 18, where the hollow member is moveable over the transducer assembly.

20. The medical device of claim 18, where the transducer assembly is advanceable out of the hollow member.

21. The medical device of claim 18, wherein said tip comprises a methylpentene copolymer.

22. The medical device of claim 18, further comprising a retaining epoxy placed adjacent to said tip to assist in retaining said tip to the device.

23. The medical device of claim 22, wherein a surface of said tip adjacent to said elongate member contains at least one groove, wherein said retaining epoxy fills said groove to increase retention of said tip.

24. The medical device of claim 22, wherein said retaining epoxy is located at least between said tip and said transducer.

25. The medical device of claim 18, wherein said elongate member comprises an insulating material.

26. The medical device of claim 18, further comprising an insulating layer over a portion of said elongate member.

27. The medical device of claim 26, wherein said energy source is an RF energy source.

28. The medical device of claim 18, wherein said hollow member comprises a material selected from the group consisting of stainless steel, titanium, and aluminum.

29. The medical device of claim 18, wherein said first and second conducting members are electrically coupled to a control unit to measure the Doppler shift between the transmitted and received signals.

30. The medical device of claim 18, wherein said transducer is a piezo-electric ultrasound transducer.

31. The medical device of claim 18, wherein further comprising a covering surrounding said transducer assembly and wherein said covering comprises a first tube.

32. The medical device of claim 31, wherein said first tube is conductive.

33. The medical device of claim 31, wherein said transducer assembly further comprises a second tube placed within said covering and having an end placed adjacent to said transducer.

34. The medical device of claim 33 wherein said second tube is conductive and where said second conducting member is electrically coupled to said second tube.

* * * * *